(12) United States Patent
Huang et al.

(10) Patent No.: US 12,027,272 B2
(45) Date of Patent: Jul. 2, 2024

(54) SYSTEM AND METHOD FOR PREDICTING DIABETIC RETINOPATHY PROGRESSION

(71) Applicant: TECHEVERST CO., LTD., Taipei (TW)

(72) Inventors: Hui-Yang Huang, Taipei (TW); Meng-Tsung Lo, Taipei (TW); Victoria Y. Wang, Taipei (TW); Pa-Chun Wang, Taipei (TW)

(73) Assignee: TECHEVERST CO., LTD., Taipei (TW)

( * ) Notice: Subject to any disclaimer, the term of this patent is extended or adjusted under 35 U.S.C. 154(b) by 463 days.

(21) Appl. No.: 17/357,227

(22) Filed: Jun. 24, 2021

(65) Prior Publication Data

US 2022/0415513 A1    Dec. 29, 2022

(51) Int. Cl.
| | |
|---|---|
| *G16H 50/30* | (2018.01) |
| *A61B 3/12* | (2006.01) |
| *G06T 7/00* | (2017.01) |
| *G16H 30/00* | (2018.01) |
| *G16H 40/67* | (2018.01) |
| *G16H 50/20* | (2018.01) |

(52) U.S. Cl.
CPC .............. *G16H 50/30* (2018.01); *A61B 3/12* (2013.01); *G06T 7/0014* (2013.01); *G16H 30/00* (2018.01); *G16H 40/67* (2018.01); *G16H 50/20* (2018.01); *G06T 2207/20081* (2013.01); *G06T 2207/20084* (2013.01); *G06T 2207/30041* (2013.01)

(58) Field of Classification Search
CPC ........ G16H 50/20; G16H 40/67; G16H 30/40; G16H 40/63; G16H 20/17; G16H 30/20; G16H 10/60; G16H 50/70; G16H 15/00; G16H 50/30; G16H 80/00; G16H 40/20; G16H 50/50; G16H 20/70; G16H 70/60; G16H 20/40; G16H 20/10
USPC ....................................................... 382/128
See application file for complete search history.

(56) References Cited

U.S. PATENT DOCUMENTS

| | | | | |
|---|---|---|---|---|
| 2021/0022606 | A1* | 1/2021 | Tanabe ................ | G06T 7/0012 |
| 2021/0228073 | A1* | 7/2021 | Park ..................... | A61B 3/0058 |
| 2022/0130047 | A1* | 4/2022 | Saha .................... | A61B 5/6821 |

* cited by examiner

*Primary Examiner* — Ajibola A Akinyemi
(74) *Attorney, Agent, or Firm* — Muncy, Geissler, Olds & Lowe, P.C.

(57) ABSTRACT

The present disclosure provides a system for predicting diabetic retinopathy progression. The system includes an image-capturing module and a processing unit. The image-capturing module is configured to capture a first fundus image of a user at a first time and a second fundus image of the user at a second time different from the first time. The processing unit is configured to receive the first fundus image and the second fundus image, compare the first fundus image and the second fundus image and indicate a difference between the first fundus image and the second fundus image. The processing unit is also configured to provide a prediction in a diabetic retinopathy progression of the user based on the difference. A method for predicting diabetic retinopathy progression is also provided in the present disclosure.

21 Claims, 8 Drawing Sheets

SYSTEM AND METHOD FOR PREDICTING DIABETIC RETINOPATHY PROGRESSION

BACKGROUND

1. Technical Field

The present disclosure relates to a system and a method for predicting diabetic retinopathy progression.

2. Description of the Related Art

Diabetic retinopathy (DR) is a microvascular disease secondary to diabetes and is one of the leading causes of vision loss. Periodic eye examinations are essential for patients with diabetes for early detection and early treatment in order to preserve vision. Currently, eye examinations are performed by health care professionals. It may be inconvenient for patients with diabetes to attend periodic eye examinations due to time, technical, and equipment constraints. In addition, there is a huge unmet need for health care professionals who are qualified to perform eye examinations, especially in rural areas. If diabetic retinopathy progression is not well monitored, it can lead to a serious decline in visual acuity.

SUMMARY

In some embodiments, a system for predicting diabetic retinopathy progression includes an image-capturing module and a processing unit. The image-capturing module is configured to capture a baseline fundus photograph of a user at a timepoint 1 and a subsequent fundus image of the same user at a timepoint 2. The processing unit is configured to receive the first fundus image and the second fundus image, compare the first fundus image and the second fundus image, and indicate a difference between the first fundus image and the second fundus image. The processing unit is also configured to provide a prediction in a diabetic retinopathy progression of the user based on the difference.

In some embodiments, a method for predicting diabetic retinopathy progression includes receiving a first fundus image of a user at a first time, receiving a second fundus image of the user at a second time different from the first time, and comparing the first fundus image and the second fundus image. The method further includes indicating a difference between the first fundus image and the second fundus image and providing a prediction in diabetic retinopathy progression of the user based on the difference.

BRIEF DESCRIPTION OF THE DRAWINGS

Aspects of some embodiments of the present disclosure are best understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1:
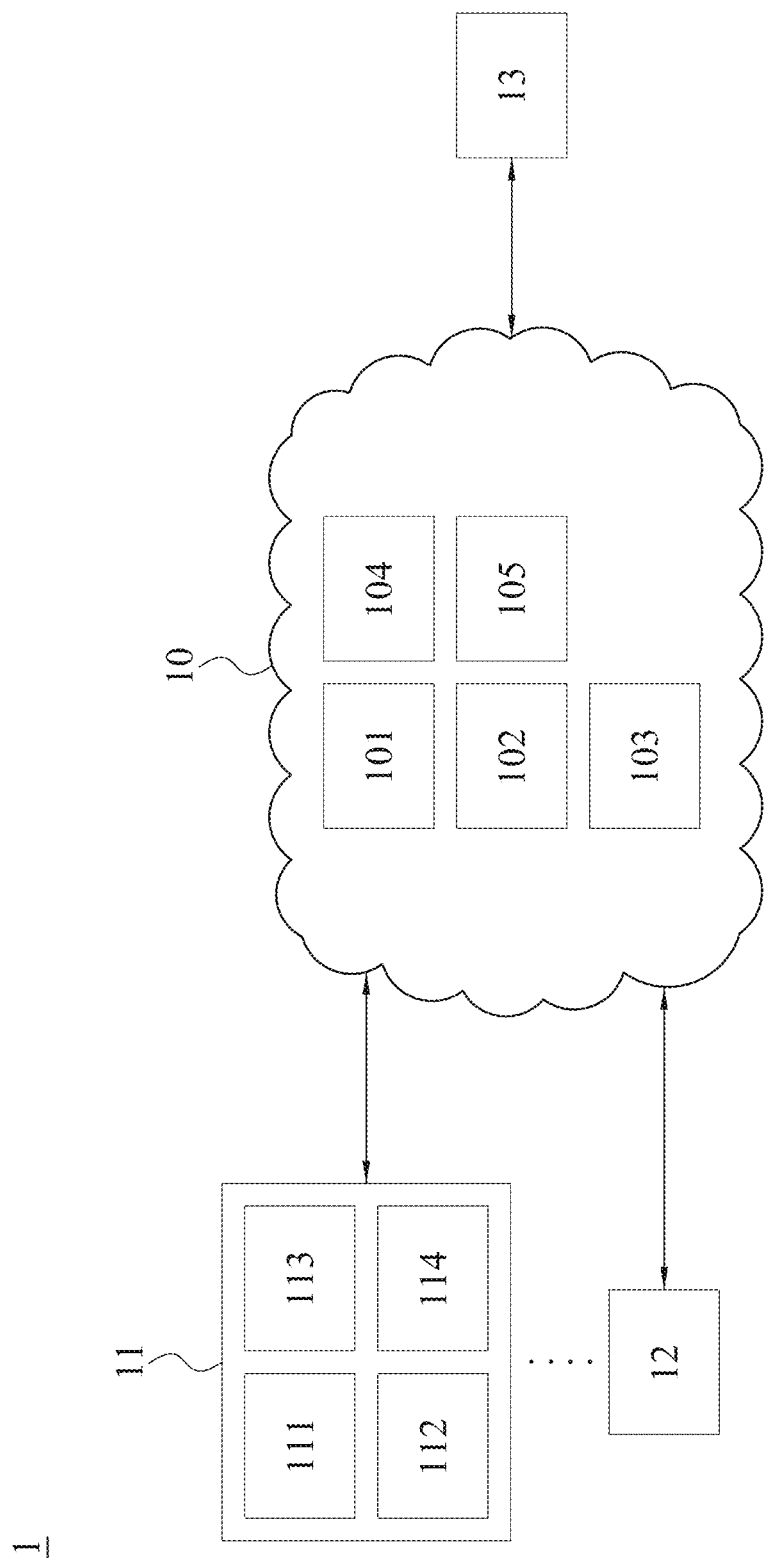
FIG. 1 is a block diagram of a system for predicting diabetic retinopathy progression in accordance with some embodiments of the present disclosure.

The following disclosure provides for many different embodiments, or examples, for implementing different features of the provided subject matter. Specific examples of components and arrangements are described as follows to explain certain aspects of the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present disclosure may be embodied as a system, method, computer program or any combination thereof. Accordingly, the present disclosure may take the form of an entirely hardware embodiment, an entirely software embodiment (including firmware, resident software, micro-code, etc.) or an embodiment combining software and hardware aspects that may all generally be referred to herein as a "unit," "module" or "system." Furthermore, the present disclosure may take the form of a computer program embodied in any tangible medium of expression having computer usable program code embodied in the medium.

The present disclosure may be described in the general context of algorithms or computer-executable instructions, such as programs, being executed by a computer. Generally, programs include routines, programs, objects, components, data structures, etc. that perform particular tasks or implement particular abstract data types. The present disclosure may also be practiced in distributed computing environments where tasks are performed by remote processing devices that are linked through a communications network. In a distributed computing environment, programs may be located in both local and remote computer storage media including memory storage devices.

FIG. 1 is a block diagram of a system 1 for predicting diabetic retinopathy progression in accordance with some embodiments of the present disclosure. The system 1 may include a data server 10, and devices 11, 12, and 13.

In some embodiments, each of the devices 11, 12, and 13 may be applied in health facilities (e.g., hospitals). The devices 11, 12, and 13 may be communicated to each other or to the data server 10 through wired or wireless techniques (e.g., Wi-Fi, cellular networks, Bluetooth, or the like). Users of the devices 11, 12, and 13 may interact via the data server 10. For examples, a patient (or any medical practitioner or medical support staff not licensed to prescribe drugs) may operate the device 11 at home. Health care workers (such as doctors, nurses, ophthalmologists, retinal specialists, or any medical practitioner licensed to prescribe drugs) may operate the device 13 at health facilities. Retinal fundus images, severity score profile over time, warning signals, and other digital information may be transmitted between the patient and the health care workers.

In some embodiments, the data server 10 may include a telemedicine platform. For example, the data server 10 may be configured to provide clinical health care remotely. In some embodiments, the data server 10 may include an image registration computation unit 101, an analysis unit 102, a memory unit 103, a warning unit 104, a communication unit 105, and a processing unit 106. In some embodiments, one or more of the units in the data server 10 may be integrated in the device 11, the device 12, and/or the device 13. In some embodiments, one or more of the units in the data server 10 may be integrated in a single device (such as a single electronic device). In some embodiments, one or more of the units in the data server 10 may be in one or more devices. The one or more devices and the device 12, and/or the device 13 may communicate with each other via wired or wireless technologies.

In some embodiments, the image registration computation unit 101 may be configured to register the retinal fundus images sent from the devices 11 and/or 12 through the communication module 114 and the communication unit 105. In some embodiments, the image registration computation unit 101 may include algorithms or computer-executable instructions, such as programs, being executed by the processing unit 106.

In some embodiments, the analysis unit 102 may be configured to analysis (such as to compare, to indicate a difference therebetween, to provide a trend or a prediction of the following images or condition). In some embodiments, the analysis unit 102 may include algorithms or computer-executable instructions, such as programs, being executed by the processing unit 106.

In some embodiments, the memory unit 103 may be configured to store data (such as retinal fundus images and severity score profile over time) or programs. In some embodiments, the memory unit 103 may include random access memory (RAM), read only memory (ROM), hard drives, as well as removable memory devices, which can include memory sticks, memory cards, flash drives, external hard drives, and so on.

In some embodiments, the warning unit 104 may be configured to generate a warning signal to the devices 11, 12, and/or 13 if an acute symptom is identified. In some embodiments, the warning unit 104 may include algorithms or computer-executable instructions, such as programs, being executed by the processing unit 106.

In some embodiments, the communication unit 105 may be configured to send/receive retinal fundus images to/from the data server 10 via wired or wireless techniques (e.g., Wi-Fi, cellular networks, Bluetooth, or the like). In some embodiments, the communication unit 105 may include a wireless communication transceiver. For example, the communication unit 105 may include a transmitter, a receiver, an antenna and so on.

In some embodiments, the processing unit 106 may be configured to execute computer-executable instructions stored in a memory such as the memory unit 103 or another medium. For example, the processing unit 106 may be configured to cause a series of operational steps to be performed on the data server 10 or other programmable apparatus to produce a computer implemented process such that the instructions provide processes for implementing the operations specified in the flowchart (described with respect to FIG. 2, FIGS. 3A to 3I, and FIG. 4). In some embodiments, the processing unit 106 may include (or may be) a processor (e.g., a central processing unit (CPU), a graphic processing unit (GPU), a micro processing unit (MCU), an application specific integrated circuit (ASIC) or the like) or a controller.

Although there are six units in the data server 10, the present disclosure is not limited thereto. For example, in some embodiments, there may be any number of units in the data server 10. In addition, in some embodiments, the data server 10 may also interact with other hardware and/or software components not depicted in FIG. 1. For example, the data server 10 may interact with one or more external user interface devices, such as a keyboard, a mouse, a display monitor, a touchscreen, etc.

In some embodiments, the device 11 may include a mobile device, such as a mobile phone or a mobile computer. In some embodiments, the device 11 may include an image-capturing module 111, a processing module 112, a memory module 113, and a communication module 114. In some embodiments, the device 11 may further include a warning receiver configured to receive a warning signal from the warning unit 104 and an indicator configured to indicate the warning signal to the user. In some embodiments, the indicator may be visual (e.g., a Light Emitting Device (LED), display, etc.), auditory (e.g., speaker, beeper, etc.) or haptic (stimulating the sense of touch). In some embodiments, the device 11 may further include display configured to display an analysis report from the data server 10.

In some embodiments, the image-capturing module 111 may include a scanner, a camera, such as a fundus camera or a camera in a mobile phone. For example, the image-capturing module 111 may include one or more lenses (such as objective lens, zoom lens, relay lens, imaging lens, condensing lens, etc.), one or more light sources (such as a low-power light source, an external light source, a near-infrared light source, etc.), a charge-coupled device (CCD), a complementary metal-oxide semiconductor (CMOS) imaging sensor, one or more signal converters (such as an analog-to-digital (A/D) converter). In some embodiments, the image-capturing module 111 may include any camera capable of photographing the interior surface of the eye, including the retina, retinal vasculature, optic disc, macula, and posterior pole (i.e., the fundus). In some embodiments, the image-capturing module 111 may be configured to capture retinal fundus photography or retinal fundus images. In some embodiments, the image-capturing module 111 may be configured to capture an ultra-wide-field (UWF) photography.

In some embodiments, the processing module 112 may include electronic integrated circuits that perform logic operations. In some embodiments, the processing module 112 may be configured to execute computer-executable instructions stored in a memory such as RAM, ROM, hard drives, removable memory devices, etc. In some embodiments, the processing module 112 may be configured to implement functions needed on the device 11. In some embodiments, the processing module 112 may have automated focus function and automated image selecting function. In some embodiments, the processing module 112 may help free the user from needing other people's assistance so that individual and elderly people can use it with ease. In some embodiments, the processing module 112 may include (or may be) a processor (e.g., a CPU, a GPU, a MCU, an ASIC or the like) or a controller.

In some embodiments, the memory module 113 may include any type of memory as described above. For example, the memory module 113 may include RAM, ROM, hard drives, removable memory devices, etc. In some embodiments, the memory module 113 may store data (such as retinal fundus images and severity score profile over time) or programs. In some embodiments, the memory module 113 may store the retinal fundus images captured by the image-capturing module 111 temporarily before the retinal fundus images are sent to the data server 10 when a communication is available.

In some embodiments, the communication module 114 may be configured to send/receive the retinal fundus images to/from the data server 10 via wired or wireless techniques (e.g., Wi-Fi, cellular networks, Bluetooth, or the like). In some embodiments, the communication module 114 may include a wireless communication transceiver. For example, the communication module 114 may include a transmitter, a receiver, an antenna and so on.

In some embodiments, one or more of the image-capturing module 111, the processing module 112, the memory module 113, the communication module 114, and the other modules or units may be a hardware and/or a software component that may be attached and fit with a mobile device such that the images may be saved locally, sent to the data server 10 for further processing, and analysis reports may be received conveniently. The device 12 and the device 13 may have configurations similar to the device 11 and will not be repeated hereafter.

Figure 2:
FIG. 2 is a flowchart of a method for predicting diabetic retinopathy progression in accordance with some embodiments of the present disclosure.

FIG. 2 is a flowchart of a method for predicting diabetic retinopathy progression in accordance with some embodiments of the present disclosure.

Referring to operation 20 in FIG. 2, a first fundus image (abbreviated as image as shown) and a second fundus image are received. In some embodiments, the images may be longitudinal data tracking the same sample (i.e., the same user's retinal) at different points in time. For example, the first image may be captured at the first timepoint, and the second image may be captured at a subsequent timepoint after the first timepoint. In some embodiments, the first image and the second image may be marked or identified with time information. For example, the first image and the second image may have a timestamp associated with a particular capturing event. In some embodiments, the time records may be used in the following operations as input values to evaluate the rate of pathologic changes and generate a severity score profile over time. In some embodiments, the first image and the second image may include image features such as colors, patterns, silhouettes, textures, diameters, geometry, locations, or other lesion features of diabetic retinopathy (will be further described with respect to operation 24).

In some embodiments, as illustrated in FIG. 1, the first image and the second image may be captured by the image-capturing module 111 and then sent to the data server 10 through the communication module 114 for more processes or analyses. In some embodiments, the first image and the second image may be stored in the memory unit 103. In some embodiments, the first image and the second image may further be sent to the device 13 for the health care workers to review through the communication unit 105. In some embodiments, the first image and the second image captured by the image-capturing module 111 may be processed or analyzed by the processing module 112. In some embodiments, the first image and the second image captured and processed or analyzed by a single device. In some embodiments, the operations 20-26 may be conducted on a single device (such as the devices 11 12 and/or 13).

In some embodiments, the first fundus image may include a baseline fundus image or a reference fundus image. The first fundus image may be a basic standard or level for the other images. In some embodiments, the second fundus image may include a subsequent fundus image taken after the first fundus image.

Figure 3A:
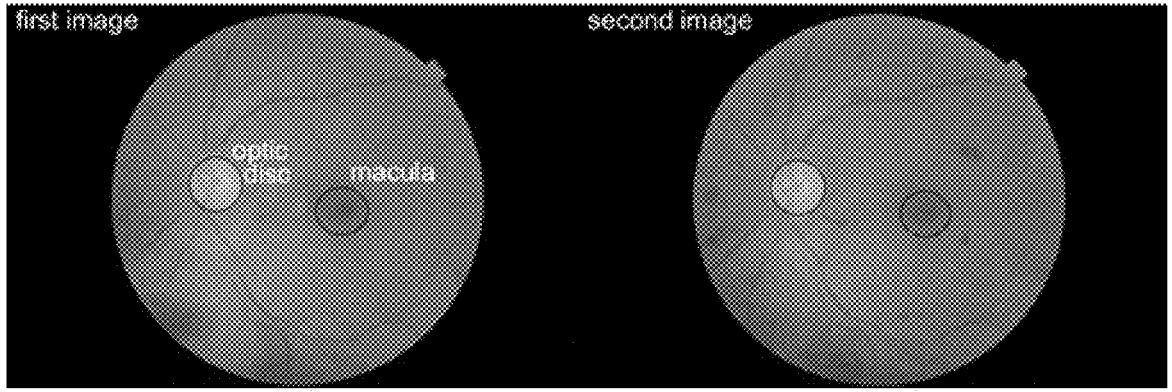
FIG. 3A are fundus images in accordance with some embodiments of the present disclosure.

In some embodiments, as shown in FIG. 3A, the image-capturing module 111 may detect the optic disc and/or macula of the retina by algorithms or computer-executable instructions to ensure that the first image and the second image are captured in the same location and in the same orientation.

Referring to operation 21 in FIG. 2, the first image and the second image are converted and normalized. In some embodiments, the first image and the second image may be converted into a CIELAB color space through, for example, an RGB/CIELAB color conversion scheme. For example, the first image and the second image may be converted into CIEL*a*b* image format. In some embodiments, the first image and the second image may be zoomed in/out, shifted, offset, or being through other calibration.

In some embodiments, the second image may be normalized with respect to the first image (and vice versa) through the following formulae:

$$L2'(x,y)=(L2-(x,y)-\text{mean}(L2))*\text{std}(L1)/\text{std}(L2)+\text{mean}(L1)$$

$$a2'(x,y)=(a2(x,y)-\text{mean}(a2))*\text{std}(a1)/\text{std}(a2)+\text{mean}(a1)$$

$$b2'(x,y)=(b2(x,y)-\text{mean}(b2))*\text{std}(b1)/\text{std}(b2)+\text{mean}(b1)$$

Paired sample points are drawn from the first image and the second image at the same locations to compute the mean and standard deviation of L, a, and b components for the first image and the second image respectively. Specifically, L1, a1, and b1 represent the converted L*a*b* notations of the reference image (i.e., the first image). L2, a2, and b2 represent the notations of the to-be-color-normalized image (i.e., the second image). L2', a2', and b2' represent the notations of the color/lighting normalized image such that the second image is normalized with a statistical distribution similar to the first image.

In some embodiments, the images (such as the first image and the second image) may be automatically converted and normalized by algorithms or computer-executable instructions and then sent to the memory unit 103 to establish a database for training the algorithms or computer-executable instructions and to establish a model to implement the system and method of the present disclosure. In some embodiments, as illustrated in FIG. 1, the first image and the second image may be converted and normalized by the analysis unit 102 of the data server 10. In some embodiments, the data server 10 may include a lighting correction unit (not shown in the figures) configured to the conduct the operation 21. In some embodiments, by converting and normalizing the images, the difference in respect of the image features may be indicated easily and correctly.

Referring to operation 22 in FIG. 2, the first image and the second image are registered. In some embodiments, the first image and the second image may be registered before the operation 21. In some embodiments, the first image and the second image may be registered by image mapping.

Figure 3B:
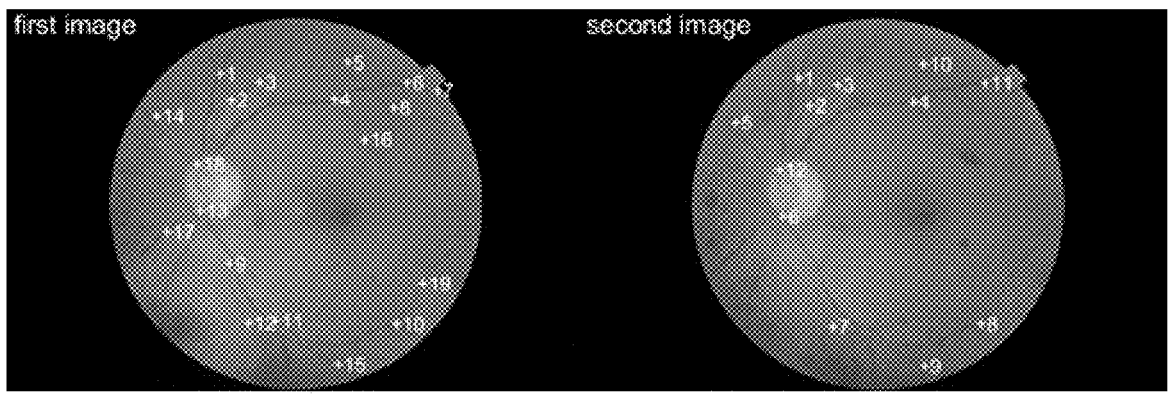
FIG. 3B are fundus images in accordance with some embodiments of the present disclosure.

In some embodiments, the first image and the second image may be overlaid and aligned with a landmark. In some embodiments, the landmark may be detected by algorithms or computer-executable instructions. For example, a corresponding image feature or a corresponding piece of information about the content of the image may be used as a landmark. In some embodiments, the corresponding image feature may be structures (such as points, edges, or objects) in the image. In some embodiments, the corresponding image feature may be vessel branching patterns. In some embodiments, the corresponding image feature may be vascular bifurcations, such as Y-shaped structures in arterioles and venules as shown in FIG. 3B. For example, the corresponding vessel branching patterns in both of the first image and the second image may be used as a landmark to register the first image and the second image.

In some embodiments, the numbers of detected Y-shaped vessel bifurcation landmarks in the first image and the second image do not need to be the same. In some embodiments, the Y-shaped vessel bifurcation landmarks in the first image do not need to be in the same order as its corresponding counterparts in the second image. In some embodiments, the proposed registration algorithm only needs four pairs of non-coplanar vessel bifurcation landmarks to get reasonably good results.

Figure 3C:
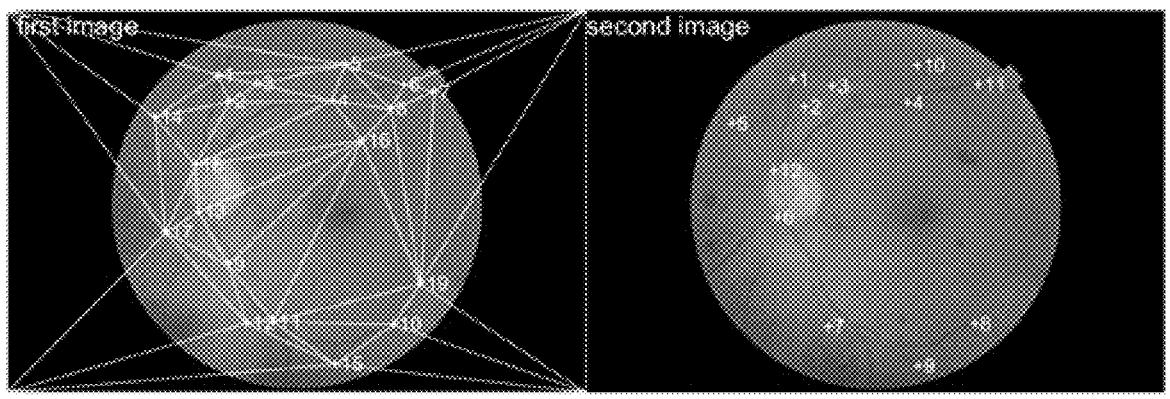
FIG. 3C are fundus images in accordance with some embodiments of the present disclosure.

In some embodiments, as shown in FIG. 3C, the Y-shaped bifurcation landmarks of the first image and four corners of the first image are processed by Delaunay triangulation to divide the rectangular image space into piecewise triangular spaces. Barycentric coordinates are built in each triangular space in the first image. For example, the barycentric coordinates (a, b, c) of the point P in triangle ABC are expressed as:

$$P(a,b,c) = a*A + b*B + c*C$$

$$a = \text{area(triangle } PBC)/\text{area(triangle } ABC)$$

$$b = \text{area(triangle } PCA)/\text{area(triangle } ABC)$$

$$c = \text{area(triangle } PAB)/\text{area(triangle } ABC)$$

$$a+b+c=1.$$

Figure 3D:
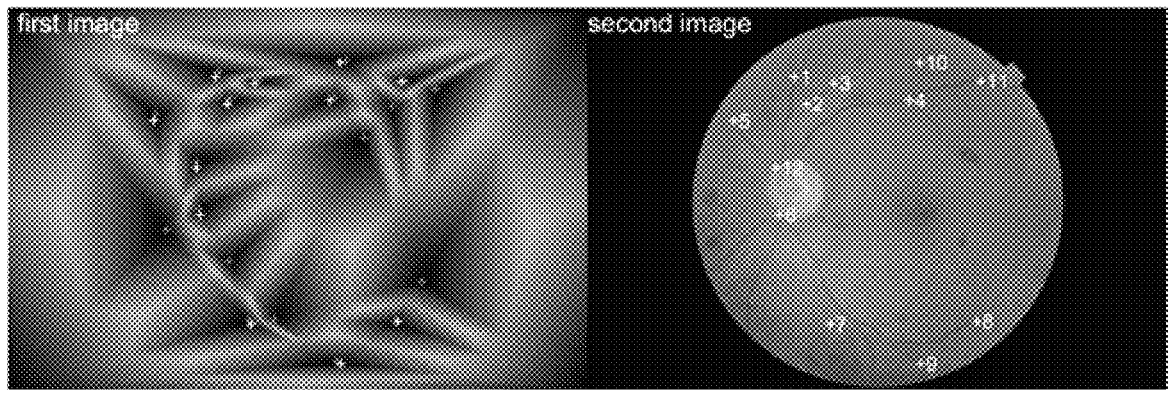
FIG. 3D are fundus images in accordance with some embodiments of the present disclosure.

In some embodiments, as shown in FIG. 3D, a piecewise linear non-negative energy field F(i, j) over the first image where the energy is the lowest at the locations of the bifurcation landmarks may be built using the following formula:

$$F(i,j) = \text{absolute}((\text{median}(a,b,c)) + \text{absolute}(\text{minimum}(a,b,c))$$

where a, b, c is the barycentric coordinates.

In some embodiments, the landmark points in the second image may be transformed by a projection transform matrix M to generate a registered second image using the following formula:

$$M\begin{bmatrix} x \\ y \\ 1 \end{bmatrix} = \begin{bmatrix} a1 & a2 & b1 \\ a3 & a4 & b2 \\ c1 & c2 & 1 \end{bmatrix}\begin{bmatrix} x \\ y \\ 1 \end{bmatrix} = \begin{bmatrix} x' \\ y' \\ 1 \end{bmatrix}$$

where a1, a2, a3, a4 control rotation; b1, b2 control translation; [c1, c2] is the projection vector.

The projection transform matrix may be solved by minimizing difference or maximizing similarity between two registered images. In some embodiments, the projection transform matrix may be solved by minimizing the summation of energy F(i, j) (defined over the first image where the energy is the lowest at the locations of the bifurcation landmarks) at the projection transformed landmarks points x', y' (which are the bifurcation landmarks at the locations x, y in the second image transformed by a projection transform matrix M). In some embodiments, the projection transform matrix may be solved by minimizing. The projection transform matrix may be solved by using any optimization strategy such as the downhill simplex algorithm.

In some embodiments, as illustrated in FIG. 1, the first image and the second image may be registered by the image registration computation unit 101 of the data server 10.

Referring to operation 23 in FIG. 2, the first image and the second image are compared to indicate or identify a difference therebetween. In some embodiments, as illustrated in FIG. 1, the first image and the second image may be compared by the image registration computation unit 101 of the data server 10 and/or the analysis unit 102 of the data server 10.

Referring to operation 24 in FIG. 2, a difference between the first image and the second image is indicated or recognized based on the comparison results of operation 23. In some embodiments, the difference may be automatically indicated or recognized by algorithms or computer-executable instructions. In some embodiments, a difference in respect of an image feature is indicated. For example, a change from the first image to the second image in respect of an image feature may be indicated.

In some embodiments, the image features may include, for example, but are not limited to, colors (e.g., red, yellow, white, etc.), patterns (e.g., beadings, patches, spots, air-fluid levels, confluence, communication, new growths, etc.), silhouettes, textures, diameters, geometry (e.g., edema, detachment, rupturing, etc.), locations (e.g., a site of a lesion), or other lesion features of diabetic retinopathy.

In some embodiments, the difference may be further automatically quantified and correlated to a pathologic change concerning the diabetic retinopathy progression by algorithms or computer-executable instructions. In some embodiments, the images (such as the first image and the second image) may be automatically characterized or labelled based on the image features and the correlated pathologic changes.

In some embodiments, pathologic changes concerning the diabetic retinopathy progression may include microaneurysm (MA), hemorrhage (including preretinal hemorrhage, intraretinal hemorrhage, vitreous hemorrhage, flame-shaped hemorrhage, dot hemorrhage, and blot hemorrhage), venous abnormality (including beading, reduplication, and looping), neovascularization, exudates (including cotton wool spots, drusen, and hard exudates), fibrosis, blood perfusion improvement, retinal ischemia, and so on.

For example, the venous beadings may be computed based on the silhouette and the texture of the images. For example, neovascularization may be detected based on the pattern of the images. For example, vascular bed fibrosis may be evaluated based on the color and the diameter of the images. For example, hard exudates may be detected based on white and/or yellow spots and edema may be graded based on the numbers and distributions of the detected hard exudates. For example, MA and hemorrhage may be detected by analyzing small red spots. For example, the blood perfusion improvement and a retinal ischemia may be derived by comparing the level of redness of between the images.

For example, color-related feature changes can be estimated by comparing the small image patches extracted from the first and second images. Smaller patches can be used to detect sharp/acute differences such as the occurrence of new acute lesions. Larger patches can be used to monitor chronic lesions between different imaging time points.

Figure 3E:
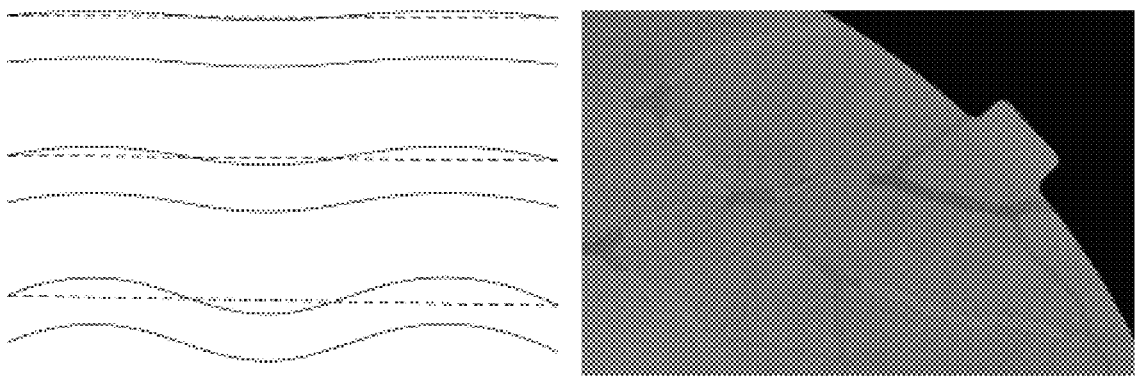
FIG. 3E is an illustration of vascular silhouette distortion in accordance with some embodiments of the present disclosure.

Vascular abnormalities such as venous beading, dilation, and distortion, and arterial shrinking can also be computed by color differences. However, early vascular changes are subtle and require more sensitive measuring approaches such as the silhouette of deformed vessels and the light reflection patterns on the beading vein's surfaces. Vascular silhouette distortion abnormality can be measured by the ratio of the distance between two points along the contour of the segmented/detected vessel and the straight distance between two points. For example, as shown in FIG. 3E, vascular silhouette distortion abnormality can be measured by the ratio of solid line distance and the dash line distance.

Figure 3F:
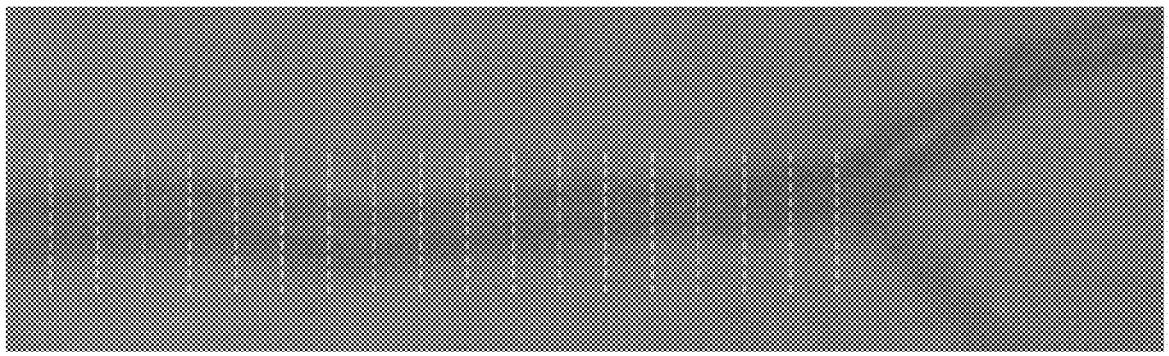
FIG. 3F illustrates a process of cross-sectional signal sampling in accordance with some embodiments of the present disclosure.
Figure 3G:
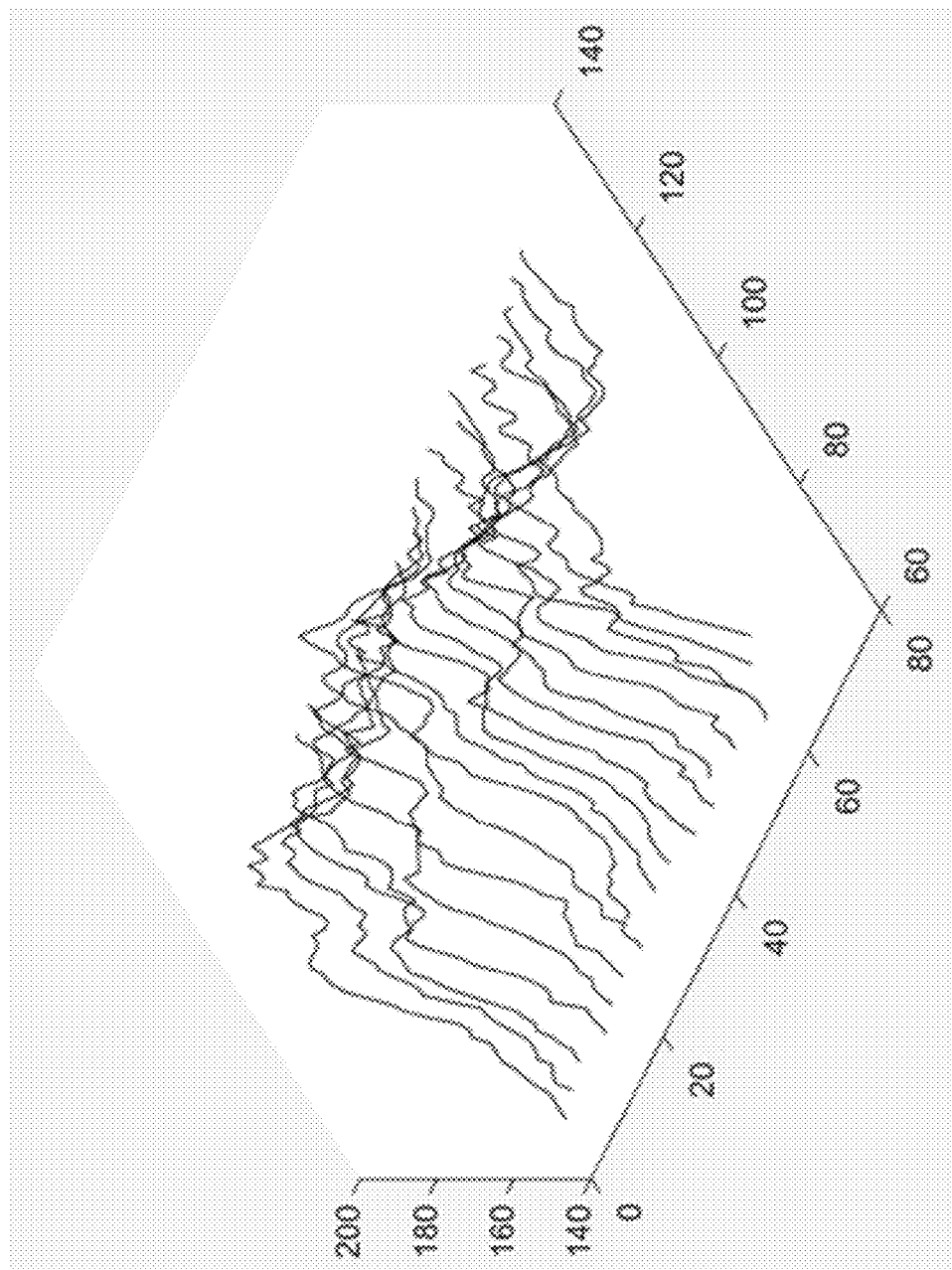
FIG. 3G illustrates intensity profile curves of cross-sectional samples in accordance with some embodiments of the present disclosure.
Figure 3H:
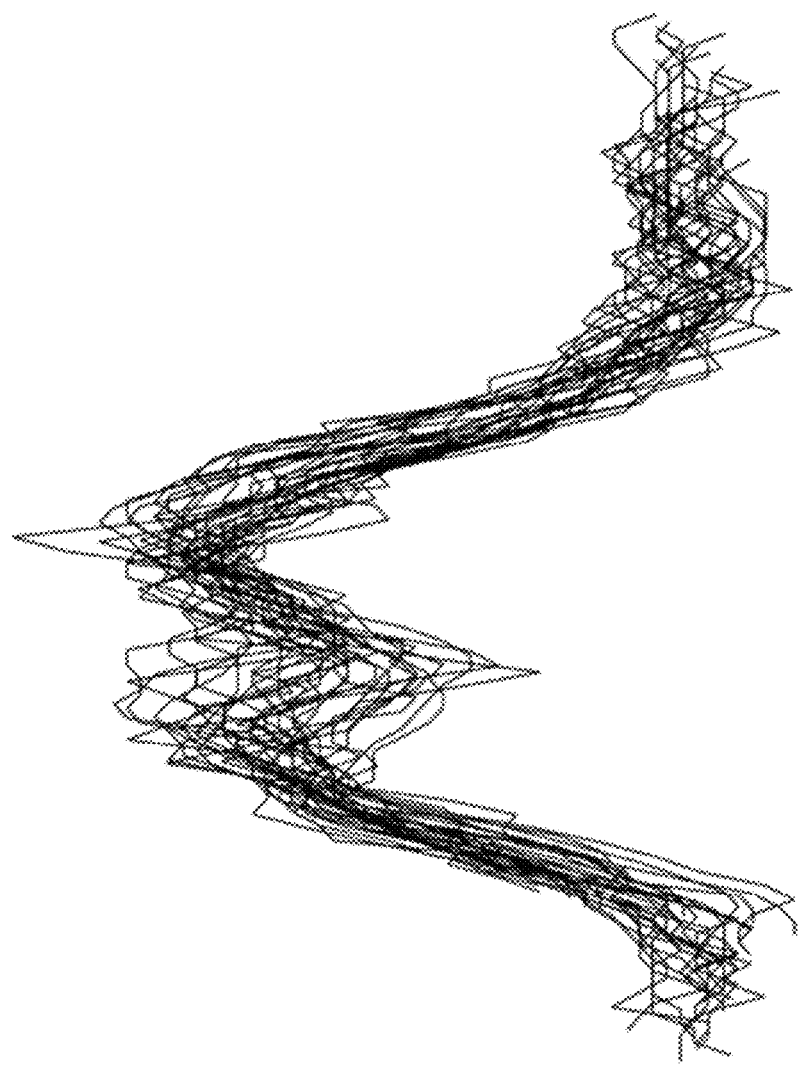
FIG. 3H illustrates a process of aligning intensity profile curves of cross-sectional samples in accordance with some embodiments of the present disclosure.

For example, cross sectional samples may be taken along the vessel to conduct vascular image texture analysis, as shown in FIG. 3F. The intensity profile curves of the samples may be aligned. For example, the intensity profile curves of the samples in FIG. 3G may be aligned as in FIG. 3H. Let $Xi(1), Xi(2), Xi(3), \ldots, Xi(N)$ represent the i-th cross sectional sample of N-intensity points, and the covariance matrix C is:

$$C = \begin{bmatrix} X1(1) & \ldots & Xi(1) \\ \vdots & \ddots & \vdots \\ X1(N) & \ldots & Xi(N) \end{bmatrix} \begin{bmatrix} X1(1) & \ldots & X1(N) \\ \vdots & \ddots & \vdots \\ Xi(1) & \ldots & Xi(N) \end{bmatrix}$$

The eigenvalues and eigenvectors of the covariance matrix C can be used to analyze the regularity of the data. The eigenvectors are the principal components, and the eigenvalues are the variances in their corresponding eigenvector directions. These eigenvalues can tell us how spread out the data is and if there exist different modes of signal patterns, which can indicate beadings. The eigenvectors of the profile signals can also be used to measure the diameters of vessel lumen for dilation and shrinking measurements between different time points.

The health of the user's retina may then be evaluated or scored according to the quantified difference and the correlated pathologic change in the subsequent operation (such as operation 25).

In some embodiments, as illustrated in FIG. 1, the difference may be indicated by the analysis unit 102 of the data server 10. In some embodiments, as illustrated in FIG. 1, the difference may be quantified and correlated to a pathologic change by the analysis unit 102 of the data server 10. In some embodiments, the data server 10 may include more than one analysis unit configured to process difference in respect of different image features. For example, the data server 10 may include a vessel analysis unit (not shown in the figures) configured to process the image features concerning the vessel. For example, the data server 10 may include a color analysis unit (not shown in the figures) configured to process the image features concerning the color. In some embodiments, other than indicating the difference by image mapping, the difference may be indicated by other methods such as dividing the images into squares and then classifying the squares by image features, using a morphological component analysis algorithm, using multi-sieving-CNN method, and so on.

Figure 4:
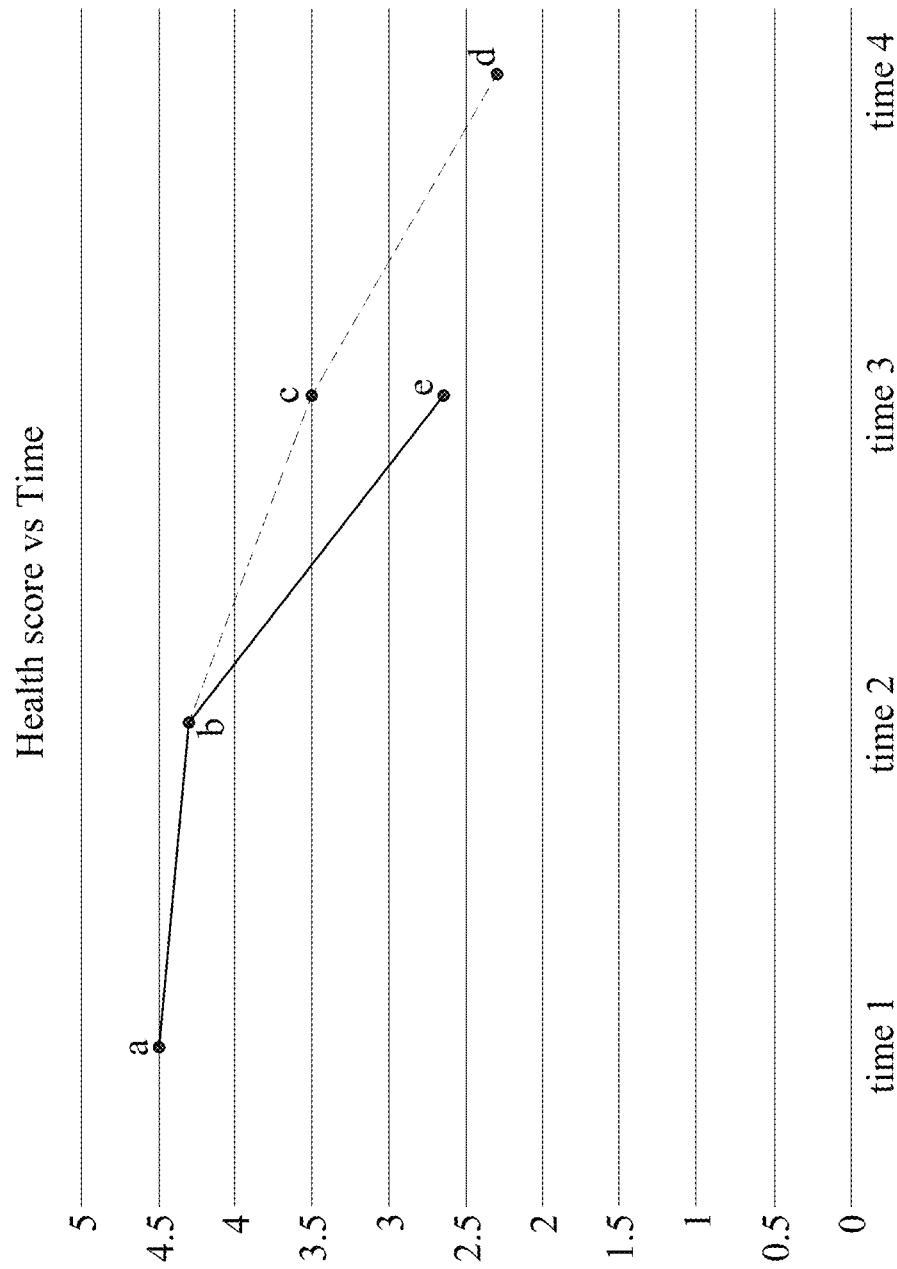
FIG. 4 is a severity score profile over time for predicting diabetic retinopathy progression in accordance with some embodiments of the present disclosure.

At operation 25, a prediction in diabetic retinopathy progression is provided. In some embodiments, based on the difference and the pathologic changes between the image and the second image obtained from operation 24, the health of the user's retina may be evaluated quantitatively using numerical scores. For example, if no abnormality is indicated or recognized in the images, the user's retina may be in good condition, and the score may be higher compared to a situation where any abnormality is observed. For example, if only MA is detected by analyzing small red spots, the score may be higher compared to a situation where another pathologic change is detected. For example, if more than 20 intraretinal hemorrhages are detected in each of 4 quadrants, the score may be higher compared to a situation where vitreous hemorrhage is detected. In some embodiments, a score profile over time as shown in FIG. 4 may be generated to express the pathologic change over time. In some embodiments, the score profile may be used to provide a prediction in diabetic retinopathy progression. In some embodiments, a higher score means the user's retina is in better condition and a lower score means the user's retina is in worse condition. However, according to some other embodiments of the present disclosure, a lower score means the user's retina is in better condition and a higher score means the user's retina is in worse condition.

In some embodiments, the prediction may include a probability and/or a time course of diabetic retinopathy progression. For example, the prediction may include a probability and/or a time course of visual deterioration. For example, the prediction may include a probability and/or a time course of a stage change of diabetic retinopathy. For example, a probability and/or a time course of the stage change (such as stage 0 to stage I, stage I to stage II, stage II to stage III, and stage III to stage IV) of diabetic retinopathy may be provided to the patient and/or the health care workers to determine the need for further intervention.

In some embodiments, the prediction may help the users to control the risk of potential visual deterioration. The users may be referred to health care workers for early detection and early treatment. Therefore, the symptoms may be alleviated and other complications may be prevented.

For example, as shown in FIG. 4, the severity scores "a" and "b" may be those derived from the first image and the second image. The severity scores "c" and "d" severity score d may be predicted. Then, a trend of diabetic retinopathy progression may be generated. If the trend of diabetic retinopathy progression is degrading, a warning signal may be generated by the warning unit 104 in the data server 10 to notify the patient and/or health care provider. In some embodiments, to determine whether a warning signal is generated, the data server 10 is programmed to score the condition of the user's retina; calculate a probability and/or a time course of diabetic retinopathy progression; and generate a warning signal when the probability and/or the time course exceed a threshold value. In some embodiments, the data server 10 is programmed to automatically generate a warning signal to the devices 11, 12, and/or 13 if the probability and/or the time course exceed a threshold value.

In some embodiments, as illustrated in FIG. 1, the retina condition may be converted into a severity score and the prediction may be provided by the analysis unit 102 in the data server 10.

In some embodiments, operation 20 to operation 24 may be repeated to receive a plurality of images and evaluate the health of the user's retina quantitatively using numerical scores from the plurality of images.

At operation 26, a warning signal may be generated. In some embodiments, a new severity score "e" may be derived from another image captured after the first image and the second image.

In some embodiments, if the score "e" is lower than the predicted severity score "c," an acute symptom is identified and a warning signal generated. In other words, the trend may be used as a standard or criteria to determine if an acute symptom is identified. In some embodiments, as illustrated in FIG. 1, the warning signal may be generated by the warning unit 104 in the data server 10. In some embodiments, the data server 10 is programmed to automatically generate a warning signal to the devices 11, 12, and/or 13 if an acute symptom is identified.

Figure 3I:
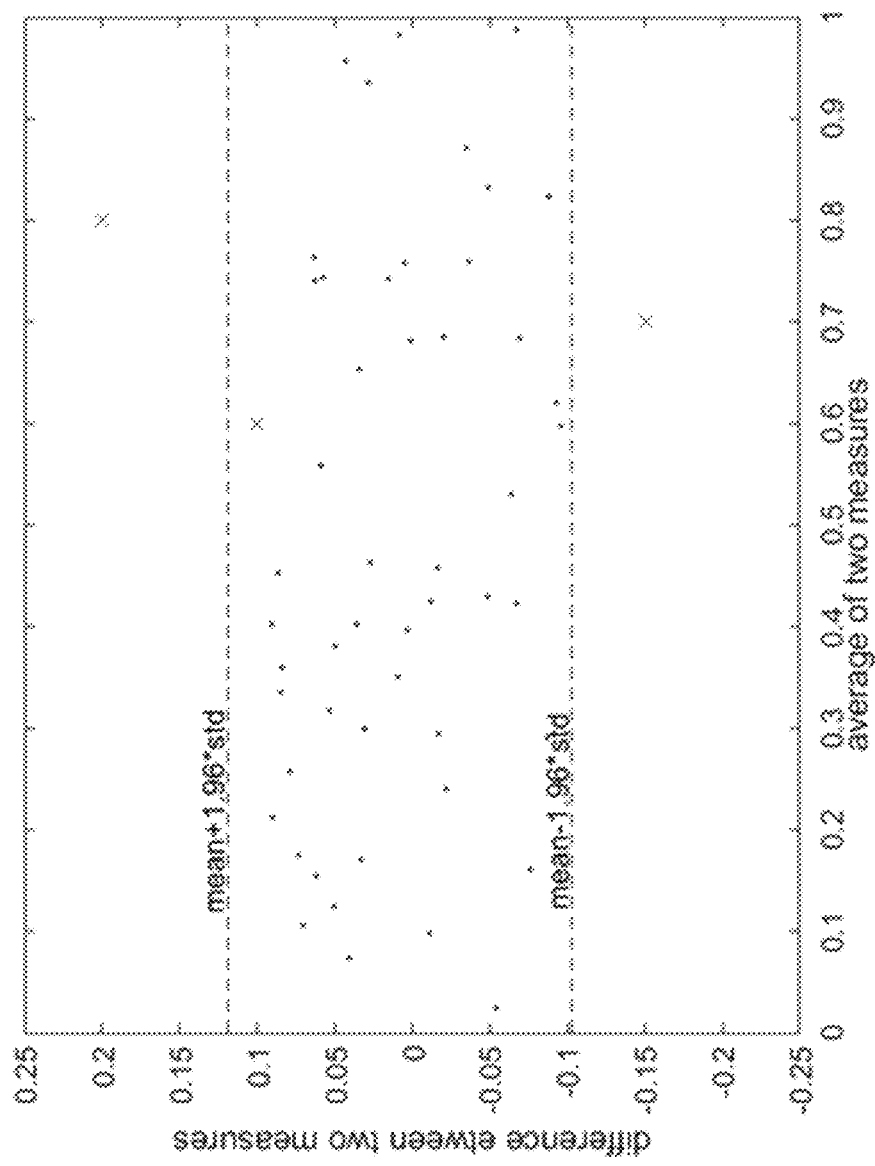
FIG. 3I is a Bland-Altman plot in accordance with some embodiments of the present disclosure.

In some embodiments, two as shown in FIG. 3I, measurements of many eyes in a database scored as stable cases may be used to create Bland-Altman plots. The significant changes (such as the acute symptom) may be assessed by using the Bland-Altman plots between two measurements at different time points. Predictions of significant changes may be defined as:

$$(m1-m2) > mean + 1.96*std$$

and/or $$(m1-m2) < mean - 1.96*std$$

where m1 and m2 are two measurements of an eye.

In some embodiments, a long-term trend may be generated by quantifying the longitudinal changes in different image features. The system and the method provided in the present disclosure may analyze the images routinely (such as daily, weekly, monthly) to provide both a long term stability monitoring capacity and also a short term emergency alarming system if any early signs of acute symptoms are detected.

For example, measures of the same eye at multiple time points (m(t1), m(t2), m(t3), m(t4), m(t5), m(t6), . . . , m(tN)) may be plotted in the Bland Altman plot as data pairs (t2, m(t1)–m(t2)), (t3, m(t1)–m(t3)), (t4, m(t1)–m(t4)), . . . , (tN, m(t1)–m(tN)) to check with the mean+/−1.96*std borderlines.

Another measure may be conducted by arranging data pairs as (t1, m(t1)), (t2, m(t2)), (t3, m(t3)), . . . , (tN, m(tN)). The trend can be estimated by moving average for regularly measuring time points using the following formula:

$$\sum_{t=ti}^{ti+n\Delta t} \frac{m(t)}{n\Delta t}$$

In some embodiments, measures of the same eye may fit with a spline model for irregular measuring time points. Combining the information of trend measurements and Bland-Altman plots comparisons can provide meaningful prediction of future improvement or possible deterioration.

In some embodiments, the images may be analyzed by characterizing image features and the correlated pathologic changes in the images by machine learning technologies or deep learning technologies. For example, the images may be characterized or labelled by a supervised learning approach, an unsupervised learning approach, or a semi-supervised learning approach. For example, the images may be labelled, unlabeled, or in the presence of both. For example, the images may be characterized or labelled using descriptors based on the image features described. In some embodiments, the images may be characterized or labelled by classification method or algorithms such as Naive Bayesian Model, decision tree, support vector machine (SVM), artificial neural network (ANN), an ensemble classifier, convolutional neural networks (CNN), deep belief networks, restricted Boltzmann machine, stacked encoders, and so on.

In some embodiments, the images may be automatically converted, normalized, and analyzed by algorithms or computer-executable instructions and then sent to the memory unit 103 to establish a model (through training the images by the classification method or algorithms described) to implement the system and method of the present disclosure. In some embodiments, the images may be divided into a training set, a validation set, and a test set. In some embodiments, the validation data may be used to monitor the model performance. In some embodiments, the model may be tuned and optimized by back propagation. In some embodiments, the model may be evaluated in a test set or an external database to assess its diagnostic performance using measures such as sensitivity, specificity and area under the curve (AUC).

In some embodiments, at least three images captured at different times of the same user may be received to build a specific profile of severity score versus time for the user and generate a prediction in diabetic retinopathy progression therefrom. In some embodiments, the three images may respectively correspond to stage I, stage II, and stage III of diabetic retinopathy, after which a stage IV may be predicted through the operations described.

Any reference in the specification to a method should be applied mutatis mutandis to a system capable of executing the method. Any reference in the specification to a system should be applied mutatis mutandis to a method that may be executed by the system.

As used herein, the singular terms "a," "an," and "the" may include a plurality of referents unless the context clearly dictates otherwise.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. There may be other embodiments of the present disclosure which are not specifically illustrated. The specification and drawings are to be regarded as illustrative rather than restrictive.

Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A system for predicting diabetic retinopathy progression, comprising:
an image-capturing module configured to capture a first fundus image of a user at a first time and a second fundus image of the user at a second time different from the first time; and
a processing unit configured to:
receive the first fundus image and the second fundus image;
detect first Y-shaped vessel landmarks in the first fundus image;
process the first fundus image by using the first Y-shaped vessel landmarks to construct a Delaunay triangulation network to divide the first fundus image into piecewise triangular spaces;
compare the first fundus image and the second fundus image;
indicate a difference between the first fundus image and the second fundus image; and
provide a prediction in a diabetic retinopathy progression of the user based on the differences.

2. The system of claim 1, wherein the processing unit is further configured to:
build a piecewise linear non-negative energy field F(i, j) over the first fundus image using a formula as follows:

$$F(i,j) = \text{absolute}((\text{median}(a,b,c)) + \text{absolute}(\text{minimum}(a,b,c))$$

where a, b, and c represent barycentric coordinates in each of the piecewise triangular spaces in the first fundus image.

3. The system of claim 2, wherein the processing unit is further configured to:
detect second Y-shaped vessel landmarks in the second fundus image;
transform the second Y-shaped vessel landmarks in the second fundus image by a projection transform matrix M as follows to generate a registered second fundus image:

$$M \begin{bmatrix} x \\ y \\ 1 \end{bmatrix} = \begin{bmatrix} a1 & a2 & b1 \\ a3 & a4 & b2 \\ c1 & c2 & 1 \end{bmatrix} \begin{bmatrix} x \\ y \\ 1 \end{bmatrix} = \begin{bmatrix} x' \\ y' \\ 1 \end{bmatrix}$$

where x and y represent coordinates of the second Y-shaped vessel landmarks, x' and y' represent transformed coordinates of the second Y-shaped vessel landmarks, a1, a2, a3, and a4 control rotation, b1 and b2 control translation, and [c1, c2] represents a projection vector.

4. The system of claim 3, wherein the projection transform matrix M is solved by minimizing a summation of a piecewise linear non-negative energy field F(i, j) at the transformed coordinates x' and y' of the second Y-shaped vessel landmarks.

5. The system of claim 3, wherein the projection transform matrix M is solved by using a downhill simplex algorithm.

6. The system of claim 1, wherein the processing unit is further configured to:
measure a vascular silhouette distortion abnormality in the second fundus image by calculating a ratio of distance between two points along a contour of a segmented vessel and a straight distance between the two points.

7. The system of claim 1, wherein the processing unit is further configured to:
predict a significant change in the second fundus image by using a Bland-Altman plot with an x-axis representing an average of two measurements and a y-axis representing a difference between the two measurements.

8. The system of claim 1, wherein the processing unit is further configured to:
correlate the difference to a pathologic change; and
generate a severity score profile over time based on the pathologic change.

9. The system of claim 1, wherein the prediction comprises a probability of the diabetic retinopathy progression.

10. The system of claim 1, wherein the prediction comprises a time course of the diabetic retinopathy progression.

11. The system of claim 1, wherein the processing unit is further configured to:
generate a trend of the diabetic retinopathy progression;
identify an acute symptom based on the trend; and
generate a warning signal if the acute symptom is identified.

12. The system of claim 1, wherein the first fundus image comprises a baseline fundus image.

13. A method for predicting diabetic retinopathy progression, comprising:
receiving a first fundus image of a user at a first time;
receiving a second fundus image of the user at a second time different from the first time;
detecting first Y-shaped vessel landmarks in the first fundus image;
processing the first fundus image by using the first Y-shaped vessel landmarks to construct a Delaunay triangulation network to divide the first fundus image into piecewise triangular spaces;
comparing the first fundus image and the second fundus image;
indicating a difference between the first fundus image and the second fundus image; and
providing a prediction in diabetic retinopathy progression of the user based on the difference.

14. The method of claim 13, further comprising:
converting the first fundus image and the second fundus image into a CIELAB color space; and
normalizing the first fundus image with respect to the second fundus image.

15. The method of claim 13, further comprising:
building a piecewise linear non-negative energy field F(i, j) over the first fundus image using a formula as follows:

$$F(i,j) = \text{absolute}((\text{median}(a,b,c)) + \text{absolute}(\text{minimum}(a,b,c))$$

where a, b, and c represent barycentric coordinates in each of the piecewise triangular spaces in the first fundus image.

16. The method of claim 15, further comprising:
detecting second Y-shaped vessel landmarks in the second fundus image;
transforming the second Y-shaped vessel landmarks in the second fundus image by a projection transform matrix M as follows to generate a registered second fundus image:

$$M \begin{bmatrix} x \\ y \\ 1 \end{bmatrix} = \begin{bmatrix} a1 & a2 & b1 \\ a3 & a4 & b2 \\ c1 & c2 & 1 \end{bmatrix} \begin{bmatrix} x \\ y \\ 1 \end{bmatrix} = \begin{bmatrix} x' \\ y' \\ 1 \end{bmatrix}$$

where x and y represent coordinates of the second Y-shaped vessel landmarks, x' and y' represent transformed coordinates of the second Y-shaped vessel landmarks, a1, a2, a3, and a4 control rotation, b1 and b2 control translation, and [c1, c2] represents a projection vector.

17. The method of claim 16, wherein the projection transform matrix M is solved by minimizing a summation of a piecewise linear non-negative energy field F(i, j) at the transformed coordinates x' and y' of the second Y-shaped vessel landmarks.

18. The method of claim 16, wherein the projection transform matrix M is solved by using a downhill simplex algorithm.

19. The method of claim 13, further comprising:
measuring a vascular silhouette distortion abnormality in the second fundus image by calculating a ratio of distance between two points along a contour of a segmented vessel and a straight distance between the two points.

20. The method of claim 13, further comprising:
predicting a significant change in the second fundus image by using a Bland-Altman plot with an x-axis representing an average of two measurements and a y-axis representing a difference between the two measurements.

21. The method of claim 13, further comprising:
providing at least three fundus images of different times of the user; and
characterizing image features in the at least three fundus images by a supervised learning approach or a semi-supervised learning approach.

* * * * *